(12) United States Patent
Ajami et al.

(10) Patent No.: US 6,989,390 B2
(45) Date of Patent: Jan. 24, 2006

(54) AMONAFIDE SALTS

(75) Inventors: Alfred M. Ajami, Brookline, MA (US); David O. Barlow, Byfield, MA (US)

(73) Assignee: Xanthus Life Sciences, Inc., Cambridge, MA (US)

(*) Notice: Subject to any disclaimer, the term of this patent is extended or adjusted under 35 U.S.C. 154(b) by 13 days.

(21) Appl. No.: 10/690,458

(22) Filed: Oct. 20, 2003

(65) Prior Publication Data

US 2004/0132763 A1  Jul. 8, 2004

Related U.S. Application Data

(63) Continuation-in-part of application No. PCT/US03/12619, filed on Apr. 22, 2003, which is a continuation-in-part of application No. 10/128,129, filed on Apr. 22, 2002, now Pat. No. 6,693,198.

(51) Int. Cl.
A61K 31/473 (2006.01)
C07D 221/14 (2006.01)
A61P 35/00 (2006.01)

(52) U.S. Cl. ............... 514/296; 514/232.8; 514/288.2; 514/253.03; 546/99; 546/100; 544/126; 544/60; 544/361

(58) Field of Classification Search ............ 546/99, 546/100; 514/296, 232.8, 228.2, 253.03; 544/126, 60, 361
See application file for complete search history.

(56) References Cited

U.S. PATENT DOCUMENTS

| 4,204,063 | A | | 5/1980 | Brana et al. |
| 4,614,820 | A | * | 9/1986 | Zee-Cheng et al. ......... 544/126 |
| 4,665,071 | A | | 5/1987 | Zee-Cheng et al. |
| 5,183,821 | A | | 2/1993 | Brana et al. |
| 5,292,881 | A | | 3/1994 | Berneth et al. |
| 5,420,137 | A | | 5/1995 | Brana et al. |
| 6,693,198 | B2 | | 2/2004 | Ajami et al. |
| 2002/0025916 | A1 | | 2/2002 | Brown |
| 2004/0132763 | A1 | | 7/2004 | Ajami et al. |

FOREIGN PATENT DOCUMENTS

| DE | 2323555 | | 8/1974 |
| DE | 2323555 | A | 8/1974 |
| ES | 533.542 | | 9/1938 |
| ES | 533.542 | | 9/1983 |
| WO | WO 01/78705 | A2 | 10/2001 |

OTHER PUBLICATIONS

Berge et al. Journal of Pharmaceutical Sciences, 1977, 66(1); 1–19.*
Braña, Miguel Fernández, and Sanz, Antonio Martínez, "Synthesis and Cytostatic Activity of Benx(de)iso–quinolin–1, 3–Diones. Structure–Activity Relationships," *Eur. J. Med. Chem.–Chimica Therapeutica* 16(3): 207–212 (1981).

Braña, F.M., "Mitonafide and Amonafide," *Ars. Pharmaceutica* 36(3):377–415 (1995).

Braña, Miguel Fernández, and Sanz, Antonio Martinez, "Synthesis and Cytostatic Activity of Benz(de)iso–quinolin–1, 3–Diones. Structure–Activity Relationships," *Eur. J. Med. Chem.–Chimica Therapeutica* 16(3): 207–212 (1981).

Braña, F.M., "Mitonafide and Amonafide," *Ars. Pharmaceutica* 36(3): 377–415 (1995).

* cited by examiner

*Primary Examiner*—Evelyn Mei Huang
(74) *Attorney, Agent, or Firm*—Hamilton, Brook, Smith & Reynolds, P.C.

(57) ABSTRACT

Disclosed is a salt of amonafide or amonafide analogs represented Structural Formula (I):

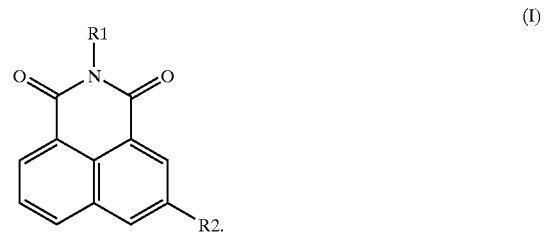

R1 is —$(CH_2)_n N^+ HR3R4$ $X^-$ or R1 is —$(CH_2)_n N^+ HR3R4$ $X^-$ or —$(CH_2)_n NR3R4$ when R2 is —$N^+ HR6R7$.

R2 is —OR5, halogen, —NR6R7, —$N^+ HR6R7$ $X^{-\prime}$ sulphonic acid, nitro, —NR5COOR5, —NR5COR5 or —OCOR5;

R3 and R4 are independently H, C1–C4 alkyl group or, taken together with the nitrogen atom to which they are bonded, a non-aromatic nitrogen-containing heterocyclic group;

each R5 is independently —H or a C1–C4 alkyl group;

R6 and R7 are independently H, C1–C4 alkyl group or, taken together with the nitrogen atom to which they are bonded, a non-aromatic nitrogen-containing heterocyclic group;

n is an integer from 0–3; and $X^-$ is the carboxylate anion of an organic carboxylic acid compound.

Also disclosed are methods of preparing certain compounds represented by Structural Formula (I).

14 Claims, 10 Drawing Sheets

AMONAFIDE SALTS

RELATED APPLICATION

This application is a continuation-in-part of International Application No. PCT/US03/12619, which designated the United States and was filed Apr. 22, 2003, published in English, which is a continuation-in-part of and claims priority to U.S. Ser. No. 10/128,129, filed Apr. 22, 2002 now U.S. Pat. No. 6,693,198. The entire teachings of the above applications are incorporated herein by reference.

BACKGROUND OF THE INVENTION

Traditional pharmaceutical process technology for manipulating the physical properties and water solubility of these important anti-cancer drug moieties has been to render them water soluble with strong mineral acids. Salt formation is reserved as the final step in the synthesis, as described by Brana and associates (U.S. Pat. No. 5,420,137; 1995) more as an after thought for formulation purposes than as an integral or even strategic component, of the reaction synthesis. Such mono and divalent mineral acid salts retain hygroscopicity, and the divalent species, which form hydrates, have also been found to be incompatible with many pharmaceutical auxiliaries required for preparing sterile injectables, tablets or gelatin capsules.

In contradistinction to the prior art and accepted practice, we have found that the early incorporation of organic acids into the synthetic elaboration of amonafide and its aminoalkyl analogs moieties permits more rapid isolation and purification of intermediates, higher concentrations of reactants during the synthetic process, and more desirable properties, such as bulk density, flocculence and compressibility.

Furthermore, the resulting organic salts show higher solubilities in water as well as in osmotically balanced electrolyte solutions, which otherwise would be incompatible via common ion effects with inorganic, mineral acid salts such as the hydrochlorides and methylsulfonates used routinely heretofore. Moreover, organic acid salts of the present invention retain a higher degree of amphiphilic compatibility both with protic and aprotic solvents of varying polarity, thereby affording a broader range of crystallizing conditions for purposes of purification and isolation than would be afforded by the corresponding mineral acid salts.

Examination of the process chemistry for amonafide readily illustrates the shortcomings of the prior art and the adverse properties of the resulting mineral salts, which have been circumvented by the present invention. Among the synthetic approaches described in the patent and professional literature, the common denominator requires acylation of 1-amino-2,2-N,N-dimethylamino ethylene diamine, or its similarly substituted homologs, with a polycyclic, substituted aryl anhydride as shown in FIG. 1. Thus for amonafide, in accordance with the method of Brana and Sanz (Eur. J. Med. Chem 16:207, 198.1) compounds I and II in FIG. 1 are combined in ethanol to afford a precipitate of mitonafide, which must then be recrystallized multiple times from a larger volume of ethanol to be freed of tarry-black or brown by-products.

While the acylation may be conducted at a concentration of 1 gram of precursor anhydride in 25 ml of solvent, recrystallization of mitonafide requires three recrystallizations at a concentration of 1 gr in 75 ml to afford light cream colored material, free of tarry substances and exhibiting a constant melting. Although the initial yields according this process range within 60–80 percent, subsequent purification reduces the net yield to 30% of material with sufficient purity for subsequent conversion into a pharmaceutically acceptable end-product.

These isolation and purification conditions also apply to the synthesis of mitonafide analogs in toluene followed by precipitation with excess gaseous hydrochloric acid, as described by Zee-Cheng and Cheng (U.S. Pat. No. 4,665,071; 1987). The mitonafide hydrochloride, of unspecified stoichiometry and hydration, obtained by this reaction is a reddish brown precipitate, containing 12% by weight of tar with no differential solubility between water and alcohol, again requiring multiple recrystallizations to afford a hydrochloride salt material of suitable quality for pharmaceutical use.

In the present invention, as shown in FIG. 1, it has now been found that the isolation of the mitonafide moiety (III) from the ethanolic reaction mixture is facilitated by admixture and complete dissolution of a suitable organic carboxylic acid compound, which upon cooling affords a near colorless adduct upon crystallization from a mother liquor which retains the preponderance of colored impurities which might otherwise have co-crystallized as in the case of the prior art. In contrast to the synthetic approach of Brana and associates (Eur. J. Med. Chem 16:207, 1981; U.S. Pat. No. 4,204,063; 1980), described hereinabove, the mitonafide is obtained directly as an organic salt, in the first step of the synthesis for the target amonafide compound, rather than post facto in accordance with the alternate teachings as in U.S. Pat. No. 5,420,137 (1995) relating to the monohydrochloride or monomethylsulfate salts of amonafide obtained by controlled titration of amonafide itself at the end of the reaction sequence.

Those skilled in the art will also recognize that salt formation of mitonafide as an isolation step as taught by U.S. Pat. No. 4,665,071 (1987) cannot be construed as an obvious precedent for the instant invention insofar as organic acids, which are the salt forming reagents in this invention are known to be insoluble in toluene, and similar non-polar solvents, even at reflux. Unlike gaseous HCl used in accordance with the prior art on mitonafide salt isolation, the organic acids of this invention are solids which can be metered with accuracy so as to achieve a precise titration stoichiometry, an elusive objective when the dispensing of gaseous acids is called for as the prevailing alternative.

The novelty of the invention described here, when contrasted to prior art, is further affirmed by the unexpected finding concerning the catalytic hydrogenolysis of the nitro substituents in the mitonafide structural skeleton.

In the specific prior art on the formation of amonafide salts, congeneric with Stucture IV in FIG. 1, Brana and associates (U.S. Pat. No. 5,420,137; 1995) fail to describe the properties of the precursor mitonafide nor do they describe the method of hydrogenation to the resulting amonafide free base. However, in prior disclosures (Spanish Patent 533,542; 1983) on a method for the industrial production specifically of amonafide, these same authors indicate that nitro reduction of the precursor mitonafide free base is effected with 10% palladium-on-carbon (Pd/C) via transfer hydrogenation in the presence of excess hydrazine under refluxing ethanolic conditions. This procedure is also summarized as the preferred approach in the chemical review literature by the same authors (Ars Pharmaceutica 36:377–415, 1995).

Those skilled in the art would recognize that such an approach could not be practiced if the mitonafide precursor were composed of a pre-formed acid salt. Under such circumstances, one might reasonably expect that the hydrazine donor reagent would be neutralized by ion exchange and become unavailable as a substrate for diimide formation, which is the active reducing species catalyzed by Pd/C. In effect, any followers of the teachings of Brana and associates would have contemplated only the use of free-base precursors rather than resorting to the less obvious alternative, namely direct reduction of a mitonafide salt as taught in this patent.

Within the larger scope of organic functional group transformations, those skilled in the art will recognize that the catalytic hydrogenation of aryl nitro compounds to the corresponding substituted anilines is usually practiced in ethanol, mixtures of ethanol and water, or in the so called universal solvents (e.g. dimethyformamide and dimethylacetamide) which are resistant to hydrogenation. Respected, classical monographs on the subject by P. N. Rylander (Catalytic Hydrogenation in Organic Synthesis, New York: Academic Press, 1979) and M. Freifelder (Practical Catalytic Hydrogenation, New York: Wiley, 1971) acknowledge that the solubility of aryl nitro compounds in general precludes use of water as the hydrogenation medium.

These experts also indicate that the preferred source of protons to effect suppression of the imine and oxime by-products of incomplete hydrogenation is achieved by admixture of the substrate with hydrochloric acid. Even in the presence of mineral acids, hydrogenations in water are poorly documented and considered idiosyncratic in both the traditional and current hydrogenation laboratory and industrial practice. Use of organic acids, such as acetic acid or formic acid, has been described, but with the caveat that dehydrative acylation will occur, thus affording the corresponding N-acyl aryl-amines as yield-lowering contaminants.

Thus, in the context of this invention, neither the specific literature on amonafide synthesis nor on methods of hydrogenation can be cited as precedent for the non-obvious chemical manipulations which were found to be advantageous here. First, the use of organic carboxylic acid compounds to effect purification and isolation of mitonafide and its analogs has not been described heretofore. Second, application of organic carboxylic acid salts of mitonafide and its analogs as direct precursors for catalytic hydrogenation has not be considered or promulgated as an effective practice. Third, the high degree of water solubility of these organic salts, itself an unexpected phenomenon, coupled with the reluctance among experts to recommend catalytic hydrogenations in water as the sole solvent, would have precluded exploration of the novel approach presented here.

Beyond these issues which demonstrate non-obviousness, there exist further practical advantages to the use of organic carboxylic acid compounds, and especially their preferred analogs, the organic carboxylic diacid compounds, in the context of this invention. The resulting aralkyl naphthalimide salts show water solubilites as high as 1:1 by proportional admixture in contrast to the mono or divalent salts of hydrochloric, methanesulfonic, or of other mineral acids, whose solubilities fall below 10% by weight. Bulk processing is facilitated for purposes of industrial synthesis, filtration, purification, and dispensing of dosage units prior to sterile filtration and lyophilization.

In dry form, these organic carboxylic acid salts show higher bulk density, porosity and compaction than their analogs mineral acid salts, while presenting lower hygroscopicity. Thus, they are more suitable for processing by direct pressing, rather than solely by granulation or agglomeration.

In terms of biological burden, the organic carboxylate anions present no electrolyte load, unlike the mineral acid anions, and are biodegradable through normal cellular pathways of intermediary metabolism. In either the case of inorganic or organic acid anions, it is a matter of record that these species provide charge balance, solubility, mechanical, adsorptive or absorptive properties to the drug moiety to which they are attached. However, it is known throughout the practice of medicinal and pharmaceutical chemistry that the salt form per se will not affect the pharmacological activity, which in the case of the polycyclic aryl and aralkylamine containing intercalator drugs is their antitumor action.

For example, in reviewing the current pharamacopoeia, the intercalator drug ametantrone is known to be equally active as the free base, hydrochloride, monoacetate and diacetate, the difference in the salt form being their bulk formulation properties. Its analog, NSC-639366, on the other hand is being developed preclinically as the fumarate salt, in preference to the hydrochloride or acetate. In the case of asulacrine, the preferred salt form is the isethionate. For crisnatol and exatecan, it is the mesylate which is pharmaceutically most suitable. Many other drug classes, with diverse modes of action, have been developed as salts of organic acids. For example, the L-malate salts of clebopride, an antinausea medication, of almotriptan, an antimigraine medication, and of pizotifen, an antihistamine, have exhibited enhanced solubility without alteration of their respective medicinal properties.

SUMMARY OF THE INVENTION

One embodiment of the present invention is a compound represented by Structural Formula (I):

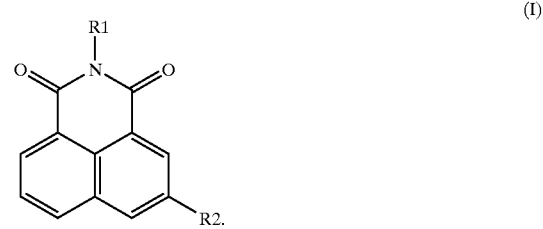

R1 is —$(CH_2)_n N^+ HR3R4$ $X^-$ or R1 is —$(CH_2)_n N^+$ HR3R4 $X^-$ or —$(CH_2)_n NR3R4$ when R2 is —$N^+ HR6R7$.

R2 is —OR5, halogen, —NR6R7, —$N^+ HR6R7$ sulphonic acid, nitro, —NR5COOR5, —NR5COR5 or —OCOR5.

R3 and R4 are independently H, C1–C4 alkyl group or, taken together with the nitrogen atom to which they are bonded, a non-aromatic nitrogen-containing heterocyclic group.

Each R5 is independently —H or a C1–C4 alkyl group.

R6 and R7 are independently H, a C1–C4 alkyl group or, taken together with the nitrogen atom to which they are bonded, a non-aromatic nitrogen-containing heterocyclic group.

n is an integer from 0–3.

$X^-$ is the carboxylate anion of an organic carboxylic acid compound. Examples of suitable organic carboxylic acids are provided below.

Another embodiment of the present invention is a pharmaceutical composition comprising a pharmaceutically acceptable carrier or diluent and a compound oh the present invention.

Another embodiment of the present invention is a method of treating a subject with cancer. The method comprises administering to the subject an effective amount of a compound of the present invention.

DETAILED DESCRIPTION OF THE INVENTION

Figure 1:
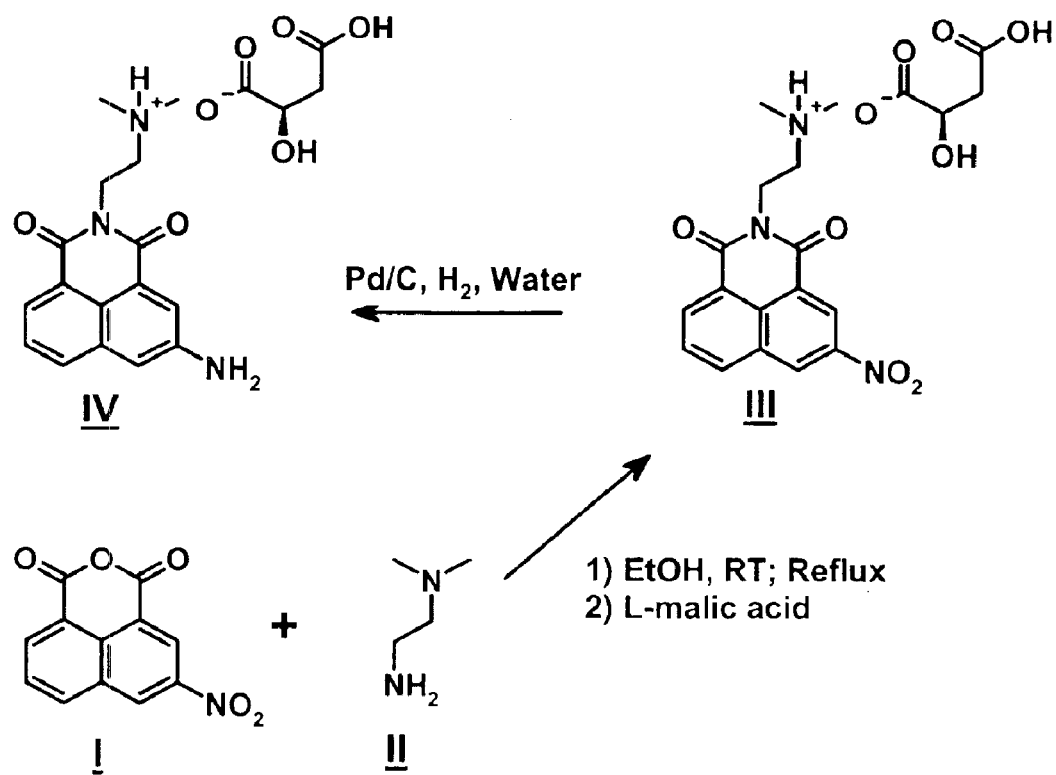
FIG. 1 is a schematic showing the synthesis of amonafide malate salt by the method disclosed herein. Many other organic carboxylic acid salts of the amonafide structural skeleton can be prepared by the method disclosed herein.

The present invention is directed to organic carboxylic acid salts of amonafide and organic carboxylic acid salts of amonafide derivatives and precursors represented by Structural Formula (I). Preferably in Structural Formula (I), n is 2; R3 and R4 are the same and are —H, —CH$_3$ or —CH$_2$CH$_3$; and R2 is —NO$_2$, —NH$_2$ or —NH$_3$$^+$X$^-$. More preferably, n is 2; R3 and R4 are —CH$_3$; and R2 is —NO$_2$, —NH$_2$ or —NH$_3$$^+$X$^-$. Suitable values for X$^-$ are provided below.

The present invention is also directed to methods of preparing organic acid salts of amonafide and derivatives represented by Structural Formula (II) by hydrogenating compounds represented by Structural Formula (III) in water. Preferably in Structural Formula (II) and (III), n is 2; R3 and R4 are the same and are —H, —CH$_3$ or —CH$_2$CH$_3$. More preferably, n is 2; and R3 and R4 are —CH$_3$. Suitable values for X$^-$ are provided below.

Most preferably, the present invention is directed to organic carboxylic acid salts of amonafide and methods of preparation therefor. The structure of amonafide is represented by Structural Formula (IV):

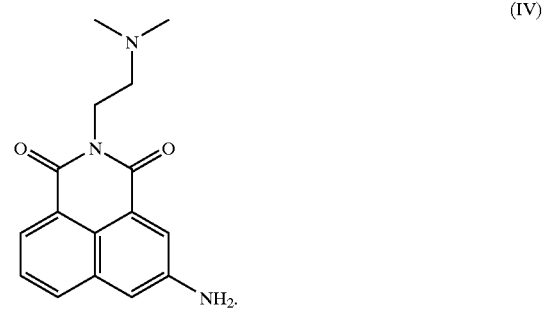

The compounds disclosed herein with two amine groups, including amonafide salts, can be monovalent, meaning that one of the amine groups is protonated, or divalent, meaning that both amine groups are protonated. A divalent compound can be protonated by two different monocarboxylic acid compounds (i.e., the two Xs in Structural Formula (I) represent two different monocarboxylic acid compounds), by two molar equivalents of the same monocarboxylic acid compound (i.e., the two Xs in Structural Formula (I) each represent one molar equivalent of the same monocarboxylic acid compound), or by one molar equivalent of a dicarboxylic acid compound (i.e., the two Xs in Structural Formula (I) together represent one dicarboxylic acid compound). Alternatively, three molar equivalents a divalent compound are protonated by two molar equivalents of a tricarboxylic acid compound. All of these possibilities are meant to be included within Structural Formulas (I) and (IV) above.

An organic carboxylic acid compound is an organic compound having one or more carbon atoms and a carboxylic acid functional group. Suitable organic carboxylic acid compounds for use in preparing the compounds of the present invention are water soluble (typically a water solubility greater than 20% weight to volume), produce water soluble salts with aryl amines and alkyl amines and have a pKa>2.0. Included are aryl carboxylic acids, aliphatic carboxylic acids (typically C1–C4), aliphatic dicarboxylic acids (typically C2–C6), aliphatic tricarboxylic acids (typically C3–C8) and heteroalkyl carboxylic acids. An aliphatic carboxylic acid can be completely saturated (an alkyl carboxylic acid) or can have one or more units of unsaturation. A heteroalkyl carboxylic acid compound is an aliphatic carboxylic acid compound in which one or more methylene or methane groups are replaced by a heteroatom such as O, S, or NH. Examples of heteroalkyl carboxylic acid compounds include a C1–C5 heteroalkyl monocarboxylic acid compound (i.e., a C2–C6 alkyl monocarboxylic acid compound in which one methylene or methane group has been replaced with O, S or NH) and C3–C8 a heteroalkyl dicarboxylic acid compound (i.e., a C2–C7 alkyl dicarboxylic acid compound in which one methylene or methane group has been replaced with O, S or NH).

An aliphatic carboxylic acid compound can be straight or branched. An aliphatic carboxylic acid can be substituted (functionalized) with, one or more functional groups. Examples include a hydroxyl group (e.g., a hydroxy C2–C6 aliphatic monocarboxylic acids, a hydroxy C3–C8 aliphatic dicarboxylic acid and a hydroxy C4–C10 hydroxy aliphatic tricarboxylic acid), an amine (e.g., an amino C2–C6 aliphatic monocarboxylic acid, an amino C3–C8 aliphatic dicarboxylic acid and an amino C4–C10 aliphatic tricarboxylic acid), a ketone (e.g., a keto C2–C6 aliphatic monocarboxylic acid, a keto C3–C8 dicarboxylic acid or a keto C4–C10 tricarboxylic acid) or other suitable functional group.

Examples of suitable organic acids are:
saturated aliphatic monocarboxylic acids such as formic acid, acetic acid or propionic acid;
unsaturated aliphatic monocarboxylic acids such as 2-pentenoic acid, 3-pentenoic acid, 3-methyl-2-butenoic acid or 4-methyl-3-pentenoic acid;
functionalized acids such as hydroxycarboxylic acids (e.g. lactic acid, glycolic, pyruvic acid, mandelic acid);
ketocarboxylic acids (e.g. oxaloacetic acid and alpha-ketoglutaric acid);
amino carboxylic acids (e.g. aspartic acid and glutamic acid);
saturated aliphatic dicarboxylic acids such as malonic acid, succinic acid or adipic acid;
unsaturated aliphatic dicarboxylic acids such as maleic acid or fumaric acid;
functionalized di- and tricarboxylic acids such as malic acid, tartaric acid, citric acid gluconic acid.
aryl carboxylic acids having sufficient water solubility, e.g., e.g., 4-hydroxybenzoic acid, salicylic acid, anthranilic acid, anisic acid and vanillic acid.

Non-aromatic nitrogen-containing heterocyclic rings are non-aromatic nitrogen-containing rings which include zero, one or more additional heteroatoms such as nitrogen, oxygen or sulfur in the ring. The ring can be five, six, seven or eight-membered. Examples include morpholinyl, thiomorpholinyl, pyrrolidinyl, piperazinyl, piperidinyl, azetidinyl, azacycloheptyl, or N-phenylpiperazinyl.

Hydrogenation of compounds represented by Structural Formula (III) is carried out under a hydrogen atmosphere at pressures between 5 and 50 pounds per square inch (psi), preferably between 13 and 17 psi. A hydrogenation catalyst is required, for example Pd/C, Pt/C, $PtO_2$, Raney Nickel and activated elemental iron or zinc. After hydrogenation, a monovalent compound is obtained. The corresponding divalent compound can be obtained by reacting the product with an additional equivalent of the same or different carboxylic acid compound.

The starting compound represented by Structural Formula (III) can be prepared by reacting the corresponding free base, i.e., where R1 is —$(CH_2)_n$NR3R4, with an organic carboxylic acid compound. Preferably, the resulting product is crystallized before hydrogenating. The free base can be prepared by reacting $H_2N(CH_2)_n$NR3R4 with 3-nitro-1,8-nitronaphthalic anhydride, wherein n, R3 and R4 are as defined in Structural Formula (I). Specific conditions for carrying out this reaction are described in U.S. Pat. No. 4,204,063, the entire teachings of which are incorporated herein by reference.

The compounds disclosed herein are useful for the treatment of in a subject. A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like). The compounds of the present invention can be used to treat a broad spectrum of cancers, including carcinomas, sarcomas and leukemias. Examples of carcinomas, including adenocarcinomas that can be treated using the compounds' of the present invention are breast, colon, lung, kidney and prostate cancers. An example of sarcomas that can be treated using the compounds of the present invention are gliomas. Examples of leukemias that can be treated using the method include Acute Myelogenous Leukemia (AML), Chronic Myelogenous Leukemia (CML), Acute Lymphocytic Leukemia (ALL) and Chronic Lymphocytic Leukemia (CLL). Preferably, the cancers that are treated using the compounds of the present invention are breast, colorectal, lung and prostate cancers.

An "effective amount" is the quantity of compound in which a beneficial clinical outcome is achieved when the compound is administered to a subject with a multi-drug resistant cancer. A "beneficial clinical outcome" includes a reduction in tumor mass, a reduction in the rate of tumor growth, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of cancer. The skilled artisan will be able to determine appropriate dosages depending on these and other factors. Effective amounts of the disclosed compounds for therapeutic application typically range between about 0.35 millimoles per square meter of body surface area (mmole/msq) per day and about 2.25 millimoles per square meter of body surface area (mmole/msq) per day, and preferably between 1 mmole/msq and 1.5 mmole/msq on five day cycles by intravenous infusion.

The disclosed compounds are administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compounds can also be administered orally (e.g., dietary), topically, by inhalation (e.g., intrabronchial, intranasal, oral inhalation or intranasal drops), or rectally, depending on the type of cancer to be treated. Oral or parenteral administration are preferred modes of administration.

The disclosed compounds can be administered to the subject in conjunction with an acceptable pharmaceutical carrier as part of a pharmaceutical composition for treatment of cancer. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrasn) are known in the art (Baker, et al., "Controlled Release of Biological Active Agents", John Wiley and Sons, 1986).

EXEMPLIFICATION

The method of the invention is illustrated in more detail by the following examples which are not intended to be limiting in any way. The course of the organic acid salt formation of amonafide and analogs thereof can be followed via the determination of the products formed by means of chromatography and NMR spectroscopy. The formed salts are further characterized by mass spectrometry and by elementary analysis.

EXAMPLE 1

Direct Synthesis of Intercalator Drug Amonafide As An Organic Acid (L-Malate) Salt by the Method of the Present Invention The following synthetic scheme is meant to describe in detail the reaction shown in FIG. 1.

1. Preparation of Mitonafide Malate (III, FW 447.42)
Reactants:
(I) 3-nitro-1,8-nitronaphthalic anhydride, (FW 243.18, CAS 3027-38-1, purity 99%, ACROS, cat. #27873-0250);
(II) N,N-dimethylethylenediamine (FW 88.15, CAS 108-00-9, purity 99%, ACROS cat. #11620-100);
L-malic acid (FW 134.09, CAS 97-67-6, purity 99% ACROS cat. #15059-1000

Synthetic Procedure:
100 gr. (0.41 mol, 1 eq.) of the anhydride (I) were combined with 1300 ml of anhydrous ethanol in a 3L 3-neck round bottom flask fitted with an adding funnel and mechanical paddle stirrer. While vigorously stirring the suspension, a solution of 40 gr (0.45 mol, 1.1 eq.) of the diamine (II) in 100 ml of anhydrous ethanol was added as a rapid drip. Stirring was continued for 12 hours (overnight), and thereafter the mixture was brought to reflux for 1 hour.

Upon cooling to an internal temperature of 80° C., a pre-warmed (also to 80° C.) solution of 60 gr. (0.42 mol, 1.09 eq.) of L-malic acid in 100 ml of ethanol was added in one portion to the reaction flask and stirring continued for 3 hours. Stirring was stopped and when the reaction reaches room temperature, the crude mitonafide malate was recovered by filtration. The solids were resuspended in 1 liter of anhydrous isopropanol, refiltered, and rinsed with diethyl ether. They were then transferred to a drying dish, triturated mechanically and vacuum desiccated in a drying oven at 0.1 Torr with heating to 30° C. for 12 hours.

A tan solid (160 gr., 87% yield) was obtained, mp 160–162° C., with a proton NMR spectrum (in perdeuterated acetic acid, 80 MHz) conforming to theory: malate-$CH_2$, 2.8 ppm, asymmetric doublet, 2H; N,N-$(CH_3)_2$, 3.1 ppm, singlet, 6H; imido-N—$CH_2$, 3.7 ppm, degenerate triplet, 2H; amino-N—$CH_2$ and malate-CH, 4.6 ppm, multiplet, 3H; aryl-CH, 8–9.3 ppm, two apparent triplets and doublet, 5H; OH, 11.4 ppm, singlet, 3H.

Material prepared in this manner was sufficiently pure for use in subsequent synthetic steps.

Alternatively, for analytical and biological samples, recrystallization was achieved by suspending the product in aqueous ethanol (water/ethanol 1/5 v/v per gram of III), heating to boil and removing any insolubles by hot filtration. Upon cooling, the mass was filtered, rinsed with diethyl ether and vacuum desiccated to afford light tan, birefringent plates (140 gr, 76% overall yield), mp 163–164° C., homogenous by HPLC, under the conditions shown in Table 1.

2. Preparation of Amonafide Malate (IV FW 417.42)
Synthetic Procedure:
A solution of 134 gr. (0.3 mole) mitonafide malate (III) was suspended in 1 liter of deionized, degassed water under an argon blanket in a Parr hydrogenation pressure bottle. 1.4 gr. of 10% Pd/C are added, and the mixture was then evacuated and purged with hydrogen gas (three times), then connected to a Parr apparatus and pressurized with hydrogen gas to 15 psi. The reaction was vigorously shaken at room temperature becoming a yellow solution instead of a tan colored suspension within two hours. It was left to hydrogenate for an additional 12 hours (overnight).

After evacuative removal of the hydrogen headspace and replacement with nitrogen, the reaction mixture was stirred with 40 gr. of activated carbon, warmed to 50° C., and passed in a Buchner funnel through filter paper overlayed with pre-washed Celite filtration aid. The filtrate was concentrated in a 2 liter round bottom flask, under reduced pressure in a rotary evaporator with a heating bath thermostated to 50° C. When a thin crust had begun to form along the meniscus of the syrupy concentrate, which weighed between 240–250 gr, the flask was refrigerated (4° C.) for 12 hrs (overnight) to permit crystallization.

The resulting mustard yellow crystals and mother liquor were triturated with isopropanol, which was added in portions to a total volume of 1 liter. After an additional 2 hrs. of refrigeration, the suspension was filtered, washed with isopropanol and diethyl ether to afford IV, 113 gr. (90%), as a mustard yellow powder, mp 182–184° C., after desiccation in a heated vacuum oven (40–50° C., 0.5 Torr, 14 hrs.). The proton NMR spectrum (in perdeuterated acetic acid, 80 MHz) conformed to theory: malate-$CH_2$, 2.8 ppm, asymmetric doublet, 2H; N,N-$(CH_3)_2$, 3.1 ppm, singlet, 6H; imido-N—$CH_2$, 3.7 ppm, degenerated triplet, 2H; amino-N—$CH_2$ and malate-CH, 4.6 ppm, multiplet, 3H; aryl-CH, 7.4–8.2 ppm, two apparent multiplets, 5H; OH, 11.4 ppm, singlet, 5H.

For comparative purposes, between and among organic salts prepared in this manner and for the purposes of subsequent Example 3, Table 3, crude reaction products were recrystalized from water/ethanol (1.5/4 v/v per gram of salt) using the minimum amount of solvent to effect dissolution at boil.

Alternatively, for analytical and bioassay samples, recrystallization was achieved by dissolving the product in water (1/4 w/v per gr. of IV) and admixing with a hot mixture of 1/1 isopropanol/methanol (1/6 w/v per gr. of IV), heating to boil and removing any insolubles by hot filtration. Upon cooling first to room temperature and then upon chilling for 12 hrs. (0–4° C.), the mass was filtered, rinsed with isopropanol followed by diethyl ether and vacuum desiccated to afford 90 gr. of mustard yellow, rhomboid crystals (85 gr., 68% overall yield), mp 184–185° C., homogenous by HPLC, under the conditions shown in Table 1.

TABLE 1

| HPLC OF MITONAFIDE AND AMONAFIDE MALATE | | | | | |
|---|---|---|---|---|---|
| | Mobile | Flow rate | Col Temp | Rt | |
| Column* | Phase** | ml/min | (° C.) | MiTm | AMFm |
| Nova Pak C18 | | | | | |
| 4 um 60 A° | 17/55/28 | 1.0 | 30 | >30 | NA |
| 3.9 × 150 mm. | 30/35/35 | 2.5 | 40 | 10.2 | 13.2 |
| | 40/25/35 | 2.5 | 40 | 5.1 | 4.7 |

TABLE 1-continued

HPLC OF MITONAFIDE AND AMONAFIDE MALATE

| Column* | Mobile Phase** | Flow rate ml/min | Col Temp (° C.) | Rt MiTm | Rt AMFm |
|---|---|---|---|---|---|
| Xterra MS C18 3.5 uM 3.0 × 150 mm. | 17/55/28 17/55/28 | 0.8 0.8 | 40 30 | 1.4 2.3 | 3.1 NA |

*End-capped (shielded) columns should be used
**CH₃CN, H₂O, MeOH v/v/v
AMFm = amonafide malate
MiTn = mitonafide malate

EXAMPLE 2

Synthesis of Amonafide Organic Carboxylic Acid Salts by Titration

The method of Example 1, illustrating the total synthesis of amonafide by a sequence of steps in which the organic acid is incorporated at the outset, can be extended to the use of organic acids other than L-malate. These can be incorporated at any stage in the synthesis scheme, where appropriate to the reaction flow and consistent with sound chemical practice. By way of convenient illustration, a panel of salts were readily prepared in semi-automated fashion. It should be understood that any analog or congener thereof, with similar aralkylamine derived basicity properties, would be equally suitable as an exemplar.

First a stock solution of amonafide free base, was dispensed into individual reaction vials so as to provide a defined amount of basic substrate. It was then titrated with a second solution containing one stoichiometric equivalent of an appropriate organic carboxylic acid, whose acidity is consistent with an aqueous pKa value of not less than 3. The resulting mixture was warmed in order to effect complete dissolution and neutralization of the species reacting ionically, and allowed to deposit the resulting salts as products upon cooling. These solutions may also be concentrated, prior to cooling, in order to optimize the reaction yield. However, for optimal results the reaction solvent in this manipulation should be selected so that the reactants are individually more soluble than their ionic combination.

In an illustrative example, the free base material was synthesized according to Brana et al in U.S. Pat. No. 5,183,821. An aliquot was dissolved in boiling anhydrous ethanol at a concentration of 1 gram per 20 ml. 10 ml of solution prepared in this manner contains 1.765 mMol of material and would, therefore, become neutralized by an equivalent amount of an appropriate organic carboxylic acid in order to afford a monovalent organic salt. Since amonafide is divalent, in theory, it can also be titrated with two equivalents of organic acid to afford a divalent salt. Thus, the number of acid equivalents that can be added should at least match the calculated minimum number of basic equivalents in the intercalator free drug and not exceed the maximum such number.

For the purpose of this example, however, salt formation has been restricted to monoequivalents, and, therefore, solutions of organic carboxylic acids containing 1.765 mMol in 10–20 ml of water at boil were prepared and added individually to each of several replicate 100 ml portions of the drug free base at the concentration and volume just described. After bringing the mixed solutions again up to boil, to insure complete dissolution of all ingredients, they were then left to cool at room temperature and refrigerated overnight, whereupon the resulting crystalline salts were harvested by filtration, dried by rinsing with diethyl ether, and desiccated under vacuum.

Table 2 provides a listing of the organic carboxylic acids that were used to titrate amonafide in order to produce the corresponding crystalline monovalent salt. Salts obtained in this manner may be characterized variously by chromatography for chemical homogeneity, and by NMR or mass spectrometry for purposes of structural characterization, as described herein above in Example 1. Characterization by elemental composition also affords a convenient method for identity verification. As shown in Table 2, the observed compositions in Part I and the theoretical elemental compositions in Part II are closely matched, demonstrating that the reaction products constitute an equimolar addition of each reactant, as would be anticipated for any such monovalent adducts of an organic base and an organic acid.

TABLE 2

| AMONAFIDE SALTS | COMPOSITION OF ORGANIC SALT | | | |
|---|---|---|---|---|
| Acid | C | H | N | O |
| Part I | | | | |
| Observed | | | | |
| A) succinic | 59.54 | 5.89 | 10.13 | 24.44 |
| B) maleic | 60.37 | 5.10 | 10.23 | 24.30 |
| C) fumaric | 59.89 | 5.52 | 10.20 | 24.39 |
| D) citric | 54.87 | 5.78 | 8.30 | 31.05 |
| E) L-tartaric | 56.27 | 4.95 | 9.23 | 29.55 |
| F) L-aspartic | 56.80 | 6.02 | 13.78 | 23.40 |
| G) pyruvic | 62.45 | 5.34 | 11.00 | 21.21 |
| H 2-oxoglutaric | 58.12 | 5.30 | 10.40 | 26.18 |
| Part II | | | | |
| Calculated | | | | |
| A) succinic | 59.84 | 5.78 | 10.47 | 23.91 |
| B) maleic | 60.14 | 5.30 | 10.52 | 24.03 |
| C) fumaric | 60.14 | 5.30 | 10.52 | 24.03 |
| D) citric | 55.58 | 5.30 | 8.84 | 30.29 |
| E) L-tartaric | 55.42 | 5.35 | 9.69 | 29.53 |
| F) L-aspartic | 57.69 | 5.81 | 13.45 | 23.05 |
| G) pyruvic | 61.45 | 5.70 | 11.31 | 21.54 |
| H 2-oxoglutaric | 58.74 | 5.40 | 9.79 | 26.08 |

Further confirmation of structural identity and purity was also obtained in each instance by NMR analysis in perdeutero acetic acid, the salt of amonafide and succinic acid being representative, in so far as it is a comparable analog to the malate salt prepared in Example 1. Thus, the salt shown prepared according to Table 2, Part I, entry A, as the monoequivalent combination of amonafide and succinic acid showed a proton NMR spectrum (in perdeuterated acetic acid, 80 MHz) conforming to theory: succinate-$CH_2$, 2.7 ppm, singlet, 6H; N,N-$(CH_3)_2$, 3.1 ppm, singlet, 6H; imido-N—$CH_2$, 3.7 ppm, degenerated triplet, 2H; amino-N—$CH_2$, 4.6 ppm, degenerated triplet, 2H; aryl-CH, 7.4–8.3 ppm, two apparent multiplets, 5H; OH, 11.4 ppm, singlet, 4H.

Although this example illustrates the use of several chiral molecules, as for example in entries E–F, it follows that suitable results for purposes of salt formation can be obtained with the corresponding racemic form or alternate antipodes of such acids. Thus, the selection of the L-enantiomers in this instance should not be taken as a restriction of the teaching; but, rather, as a case in point that would be understood by those practiced in the art to be the most commonly available such organic carboxylic acid forms suitable for purposes of biological experimentation.

EXAMPLE 3

Organic Salts of Amonafide are More Readily Purified than HCL or Methanesulfonic Acid Salts of Amonafide Independent of Method of Synthesis I. Direct Synthesis Amonafide Monohydrochloride Salt by the Method of Example 1

1. Preparation of Mitonafide Monohydrochloride (FW 349.82)

Reactants:
(I) 3-nitro-1,8-nitronaphthalic anhydride, (FW 243.18, CAS 3027-38-1, purity 99%, ACROS, cat. #27873-0250);
(II) N,N-dimethylethylenediamine (FW 88.15, CAS 108-00-9, purity 99%, ACROS cat. #11620-100);
6.0 N Hydrochloric acid (FW 36.45 CAS 7647-01-0, purity 99.9% ACROS cat. #61327-0010

Synthetic Procedure:

10 gr. (0.041 mol, 1 eq.) of the anhydride (I) were combined with 130 ml of anhydrous ethanol in a 0.3L 3-neck round bottom flask fitted with an adding funnel and mechanical paddle stirrer. While vigorously stirring the suspension, a solution of 4 gr (0.045 mol, 1.1 eq.) of the diamine (II) in 10 ml of anhydrous ethanol was added as a rapid drip. Stirring was continued for 12 hours (overnight), and thereafter the mixture was brought to reflux for 1 hour.

Upon cooling to an internal temperature of 80° C., a pre-warmed (also to 80° C.) solution of 7.5 ml of 6.0 N HCl (0.045 mol, 1.1 eq.) and 2.5 ml of ethanol was added in one portion to the reaction flask and stirring continued for 3 hours. Stirring was stopped and when the reaction reaches room temperature, the crude mitonafide monohydrochloride was recovered by filtration. The solids were resuspended in 0.1 liter of anhydrous isopropanol, refiltered, and rinsed with diethyl ether. They were then transferred to a drying dish, triturated mechanically and vacuum desiccated in a drying oven at 0.1 Torr with heating to 30° C. for 12 hours.

A tan solid (11.9 gr., 83% yield) was obtained, which on recrystallization from water ethanol, 2:1 v/v, afforded 8.3 gr, mp 180–183° C. homogenous by HPLC, under the conditions described in Example I.

2. Preparation of Amonafide Monohydrochloride (FW 319.79)

A solution of 10.5 gr. (0.03 mole) mitonafide monohydrochloride was suspended in 0.1 liter of deionized, degassed water under an argon blanket in a Parr hydrogenation pressure bottle. 0.15 gr. of 10% Pd/C are added, and the mixture was then evacuated and purged with hydrogen gas (three times), then connected to a Parr apparatus and pressurized with hydrogen gas to 15 psi. The reaction was vigorously shaken at room temperature becoming a yellow solution instead of a tan colored suspension within two hours. It was left to hydrogenate for an additional 12 hours (overnight).

After evacuative removal of the hydrogen headspace and replacement with nitrogen, the reaction mixture was stirred with 4 gr. of activated carbon, warmed to ° C., and passed in a Buchner funnel through filter paper overlayed with pre-washed Celite filtration aid. The filtrate was concentrated in a 0.25 liter round bottom flask, under reduced pressure in a rotary evaporator with a heating bath thermostated to 50° C. When a thin crust had begun to form along the meniscus of the syrupy concentrate, which weighed between 23–24 gr, the flask was refrigerated (4° C.) for 12 hrs (overnight) to permit crystallization.

The resulting mustard yellow crystals and mother liquor were triturated with isopropanol, which was added in portions to a total volume of 0.1 liter. After an additional 2 hours of refrigeration, the suspension was filtered, washed with isopropanol and diethyl ether to afford 7.9 gr. (81%), as a mustard yellow powder, mp 184–88° C., after desiccation in a heated vacuum oven (40–50° C., 0.5 Torr, 14 hrs.). However, the material was non-homogenous by HPLC, under the conditions shown in Table 1, revealing a main fraction consisting 91% of the peak areas and at last 4 additional impurities ranging in areas from 0.5 to 4.5% of the total analyte areas.

Recrystallization was achieved by dissolving the product in water (1/20 w/v per gr.) and admixing with a hot mixture of 1/1 isopropanol/methanol (1/20 w/v), heating to boil and removing any insolubles by hot filtration. Upon cooling first to room temperature and then upon chilling for 12 hrs. (0–4° C.), the mass was filtered, rinsed with isopropanol followed by diethyl ether and vacuum desiccated to afford mustard yellow needles (6.3 gr., 65% overall yield), mp 289–290° C. Chromatographic analysis revealed the recrystallized material to be 97.3% pure and containing an impurity of 1.6%, consisting of the incompletely hydrogenated. A second recrystalization afforded 4.2 (52% overall yield) grams of material with a purity of 99.1%.

As shown in Table 3, the yield and the need for additional recrystallization steps offer a clear contrast to the results of the congeneric synthesis of organic acid salts of amonafide, e.g. amonafide L-malate from mitonafide L-malate. The latter affords purer product in fewer steps, and with a lower solvent volume.

II. Preparation of Amonafide Malate by the Method of Example 1

Amonafide malate, amonafide fumarate, amonafide maleate, amonafide malonate and amonafide hemisuccinate were prepared according to the method of Example 1. In the case of succinic acid, the organic acid was dispensed as a half-equivalent in order to generate mitonafide hemisuccinate. This method is illustrated schematically in FIG. 1 for amonafide malate. Crude product that was isolated from the hydrogenation reaction mixture was analyzed for purity by high pressure liquid chromatography (HPLC) according to the conditions described in Table 1 above. The crude product was recrystallized from water/ethanol (1.5/4 v/v) using the minimum amount of solvent required to dissolve the crude product at boil, which is shown in the last column of Table 3 for each salt. The recrystallized product was then analyzed for purity by HPLC. The purity for the isolated and recrystallized salts are reported below in Table 3.

III. Preparation of Organic Acid Salts of Amonafide by Either Method of Example 1 or Method of Example 2

As shown in the second column of Table 3 below, fumarate, malate, maleate, malonate and hemi-succinate salts of amonafide were obtained according to the procedures described in Example 1 by in situ formation of the corresponding mitonafide salt, followed by catalytic hydrogenation. Also, the adipate, aspartate, citrate, glycolate, malate, oxoglutarate, pyruvate, salicylate, succinate, and tartrate salts of amonafide were obtained according to the procedures described in Example 2 from the crude amonafide free base prepared as described above in the previous paragraph. The purities of the crude salts were assessed by HPLC according to the conditions described in Table 1 above. The crude salts were then recrystallized from the minimum amount of water/ethanol (1.5/4 v/v) using the minimum amount of solvent required to dissolve the crude product at boil, which is shown in the last column of Table 3 for each salt. The resulting purified salts were again assessed for purity. The purity for the crude and recrystallized salts are shown in Table 3 below.

IV. Preparation of the Hydrochloride Salt and Methanesulfonic Acid Salt of Amonafide the Method of Brana et al., U.S. Pat. No. 5,420,137

1. Preparation of Amonafide Free Base

Amonafide free base was prepared according to procedures disclosed in U.S. Pat. No. 5,183,821 to Brana et al. Exemplary conditions, at $\frac{1}{100}^{th}$ the reported scale, are as follows: 30 g of 2-(2-dimethylaminoethyl)-5-nitrobenzo[d,e]isoquinoline-1,3-dione and 0.75 gr. of 10% palladium on carbon in 750 milliliters of ethanol were refluxed with stirring until complete dissolution of the nitro compound. Thereupon 40 milliliters of hydrazine hydrate, meeting current commercial specifications of 60% anhydrous hydrazine equivalence, were added slowly over a 30 minute period. When addition was complete, reflux and stirring were continued for 3.5 hours, followed by filtration while still hot. The reaction mixture was left overnight to reach room temperature. The crystalline product was then filtered to afford amonafide free base.

2. Preparation of Amonafide Hydrochloride and Methanesulfonic Salts.

The hydrochloride and methanesulfonic acid salts of amonafide were prepared according to U.S. Pat. No. 5,420,137. Exemplary procedures are as follows: 3 g of crude amonafide free base, obtained as described in the previous two paragraphs, above, were dissolved under reflux in 60 ml of virtually anhydrous ethanol. Subsequently 1 ml of 35% (1 equivalent, estimated) strength hydrochloric acid was added dropwise while shaking vigorously. After cooling, the resulting crystals were filtered off and washed with 10 ml of anhydrous ethanol. The methanesulfonic acid salt was obtained using the same procedure, but replacing hydrochloric acid with 0.8 ml of methanesulfonic acid. The purity was assessed by HPLC using the conditions described in Table 1. The isolated products were then recrystallized from water/ethanol (1.5/4 v/v) using the minimum amounts of solvent required to dissolve the crude product at boil, which are shown for each salt in Table 3. The resulting purified salts were again assessed for purity. The results are shown in Table 3 below.

V. Preparation of the Hydrochloride Salt of Amonafide by the Method of Zee-Chang et al., U.S. Pat. No. 4,614,820

The hydrochloride salt of amonafide was obtained by the method of Zee-Chang et al., U.S. Pat. No. 4,614,820. Exemplary conditions are as follows: a mixture of the hydrochloride salt of N-(dimethylaminoethyl)-3-nitro-1,8-naphthalimide and 10% palladium-on-charcoal in water was hydrogenated at room temperature under 40 lbs/in$^2$ of hydrogen for one hour. The theoretical amount of hydrogen was absorbed. To the mixture was added 3 ml of concentrated hydrochloric acid. It was then filtered and the filtrate was evaporated to dryness under reduced pressure. The residue was triturated with 30 ml of absolute ethanol and filtered. The resulting solid was then washed with ether and dried. The purity was assessed by HPLC using the conditions described in Table 1. The crude product was then recrystallized from water/ethanol (1.5/4 v/v) using the minimum amount of solvent (40 mL/g) required to dissolve the crude product at boil. The resulting purified salts were again assessed for purity. The results are shown in Table 3 below.

VI. Indirect Synthesis of Amonafide Monohydrochoride via Salt Exchange from Presursor Amonafide Malate 1. Preparation of Amonafide Free Base.

A batch of amonafide L-malate was prepared in accordance with the method of Example I. The material so obtained was 99.4% chromatographically pure on a 10 gram synthetic scale, consistent with previous findings on the larger scale. The material was then converted to the free base amonafide, as follows: 10 grams of the L-malate salt were dissolved in 100 ml distilled water and titrated with vigorous stirring to pH 7 by the addition of ¼ concentrated ammonium hydroxide. The large mass of yellow needles that formed was filtered by suction, washed with water, and recrystalized from ethanol to afford 5.8 gr. Of 99.8% chromatographically pure amonafide free base, mp 172° C. (MW 283.3, 93% yield).

2. Preparation of Amonafide Monohydrochloride

The free base was converted into the monohydrochloride by suspending 5 gr in 10 ml of water and adding 1 equivalent of 6.0 normal (2.9 ml) with vigorous stirring and warming. Upon dissolution, 20 ml of boiling ethanol are added slowly to the clouding point, and the mixture allowed to cool and deposit crystals, which are then harvested by filtration at room temperature, rinsed with ethanol and ether, and vacuum dried to afford 5.4 grams of product, mp 292° C. The amonafide monohydrochloride prepared by the method of salt exchange was found to be 99.2% chromatographically pure and free of any detectable N-hydroxylamine. Notwithstading this level of purity, the amonafide monohydrochloride prepared by salt exchange showed low solubility when included in the test panel shown in Tables 3 and 4.

TABLE 3

| Salt | Method | Purity (from reaction pot) | Purity (after 1 × crystallization) | Solvent (ml/g) |
|---|---|---|---|---|
| Amonafide Malate | Example 1 | 92% | 99.3% | 7.5 |
| Amonafide Malate | Example 2 | 98% | 99.6% | 7.5 |
| Amonafide HCl | U.S. Pat. No. 5,420,137 to Brana et al. | 76% | 94% | 40 |
| Amonafide HCl | U.S. Pat. No. 4,614,820 to Zee-Cheng, et al. | 74% | 92% | 40 |
| Amonafide HCl | Example 1 | 93% | 97.3% | 40 |
| Amonafide HCl | Salt exchange | N/A | 99.2% | 40 |
| Amonafine methanesulfonate | U.S. Pat. No. 5,420,137 to Brana et al | 86% | 93% | 25 |
| Amonafide tartrate | Example 2 | 90% | 99.2% | 20 |
| Amonafide Adipate | Example 2 | 89% | 98% | 25 |
| Amonafide Aspartate | Example 2 | 78% | 98.7% | 30 |
| Amonafide Citrate | Example 2 | 92% | 99.1% | 25 |
| Amonafide Fumarate | Example 1 | 76% | 98.9% | 25 |
| Amonafide glycolate | Example 2 | 92% | 99.3% | 12.5 |
| Amonafide maleate | Example 1 | 70% | 99.2% | 20 |
| Amonafide malonate | Example 1 | 74% | 97% | 20 |
| Amonafide 2-oxoglutarate | Example 2 | 77% | 98.1% | 30 |
| Amonafide pyruvate | Example 2 | 84% | 99.5% | 20 |
| Amonafide salicylate | Example 2 | 87% | 98.7% | 35 |
| Amonafide hemi-succinate* | Example 1 | 88% | 98.7% | 15 |

TABLE 3-continued

| Salt | Method | Purity (from reaction pot) | Purity (after 1 × crystallization) | Solvent (ml/g) |
|---|---|---|---|---|
| Amonafide succinate | Example 2 | 93% | 99.2% | 20 |
| Amonafide L-tartrate | Example 2 | 90% | 99.2% | 20 |

*hemisuccinate prepared from mitonafide hemisuccinate, wherein 0.5 equivalents of succinic acid were used in the mitonafide isolation. By contrast, the succinate salt is prepared when admixing one equivalent.

As is evident from the data shown in Table 3, the purity of recrystallized organic acid salts of amonafide was in every case significantly greater than the corresponding recrystallized hydrochloric acid salt and methanesulfonic acid salt. Moreover, in comparing the malate to the HCl moieties, the recrystallization volume for purification of the malate salt was 5 times smaller, indicating both greater solubility in hydroxylic media and also greater ease of handling in a concentrated solution. The glycolate and hemisuccinate salts were also significantly more soluble than either the HCl or methanesulfonic acid salt.

EXAMPLE 4

Organic Acid Salts of Amonafide are More Soluble in Water than the Corresponding Hydrochloride Salt Independent of Method of Synthesis A number of organic acid amonafide salts of the present invention were tested for their solubility in aqueous medium and compared with the solubility of the corresponding hydrochloride and methansolufonic acid salts. Specifically, solubility assessment (in duplicate) for the salt survey was conducted by dissolving, or attempting to dissolve, 50, 100 and 200 mg of each salt in 1 ml of USP water or 1 ml of isotonic saline by vortexing at ambient temperature. Solutions were allowed to equilibrate for 1 hour, their dissolution status noted, and then refrigerated for an additional hour (at 2° C.). Thereafter, the samples were returned to room temperature and examined for precipitate formation and allowed to equilibrate for another hour until a final inspection for dissolution status. Results are presented in Table 4.

TABLE 4

| AMONAFIDE SALT | Amount of Amonafide Salt (mg) | Solvent | Timepoint | Dissolution Status |
|---|---|---|---|---|
| L-Aspartate | 100 | 0.9% Sodium chloride (saline) | 0 hours | Soluble |
|  |  | Distilled Water | 1 hours | Soluble |
|  |  |  | 0 hours | Soluble |
|  |  |  | 1 hours | Soluble |
|  | 200 | 0.9% Sodium chloride (saline) | 0 hours | Partially soluble |
|  |  | Distilled Water | 1 hours | Partially soluble |
|  |  |  | 0 hours | Partially soluble |
|  |  |  | 1 hours | Partially soluble |
| Citrate | 50 | 0.9% Sodium chloride (saline) | 0 hours | Insoluble |
|  |  | Distilled Water | 1 hours | Insoluble |
|  |  |  | 0 hours | Insoluble |
|  |  |  | 1 hours | Insoluble |
| Fumarate | 50 | 0.9% Sodium chloride (saline) | 0 hours | Insoluble |
|  |  | Distilled Water | 1 hours | Insoluble |
|  |  |  | 0 hours | Insoluble |
|  |  |  | 1 hours | Insoluble |
| Maleate | 50 | 0.9% Sodium chloride (saline) | 0 hours | Insoluble |
|  |  | Distilled Water | 1 hours | Insoluble |
|  |  |  | 0 hours | Insoluble |
|  |  |  | 1 hours | Insoluble |
| Malonate | 50 | 0.9% Sodium chloride (saline) | 0 hours | Soluble |
|  |  | Distilled Water | 1 hours | Soluble |
|  |  |  | 0 hours | Soluble |
|  |  |  | 1 hours | Soluble |
|  | 100 | 0.9% Sodium chloride (saline) | 0 hours | Insoluble |
|  |  | Distilled Water | 1 hours | Insoluble |
|  |  |  | 0 hours | Insoluble |
|  |  |  | 1 hours | Insoluble |
| Methanesulfonate | 200 | 0.9% Sodium chloride (saline) | 0 hours | Soluble |
|  |  | Distilled Water | 1 hours | Soluble |
|  |  |  | 0 hours | Soluble |
|  |  |  | 1 hours | Soluble |

TABLE 4-continued

| AMONAFIDE SALT | Amount of Amonafide Salt (mg) | Solvent | Timepoint | Dissolution Status |
|---|---|---|---|---|
| 2-Oxo-glutarate | 50 | 0.9% Sodium chloride (saline) | 0 hours | Soluble |
| | | Distilled Water | 1 hours | Soluble |
| | | | 0 hours | Soluble |
| | | | 1 hours | Soluble |
| | 100 | 0.9% Sodium chloride (saline) | 0 hours | Insoluble |
| | | Distilled Water | 1 hours | Insoluble |
| | | | 0 hours | Insoluble |
| | | | 1 hours | Insoluble |
| Succinate | 50 | 0.9% Sodium chloride (saline) | 0 hours | Insoluble |
| | | Distilled Water | 1 hours | Insoluble |
| | | | 0 hours | Soluble |
| | | | 1 hours | Soluble |
| | 100 | 0.9% Sodium chloride (saline) | 0 hours | Insoluble |
| | | Distilled Water | 1 hours | Insoluble |
| | | | 0 hours | Insoluble |
| | | | 1 hours | Insoluble |
| mono-Hydrochloride by the method of Example 1 | 50 | 0.9% Sodium chloride (saline) | 0 hours | Partially soluble |
| | | Distilled Water | 1 hours | Partially soluble |
| | | | 0 hours | Partially soluble |
| | | | 1 hours | Partially soluble |
| | 100 | 0.9% Sodium chloride (saline) | 0 hours | Insoluble |
| | | Distilled Water | 1 hours | Insoluble |
| | | | 0 hours | Partially soluble |
| | | | 1 hours | Insoluble |
| | 200 | 0.9% Sodium chloride (saline) | 0 hours | Insoluble |
| | | Distilled Water | 1 hours | Insoluble |
| | | | 0 hours | Insoluble |
| | | | 1 hours | Insoluble |
| mono-Hydrochloride by the method of salt exchange | 50 | 0.9% Sodium chloride (saline) | 0 hours | Partially soluble |
| | | Distilled Water | 1 hours | Partially soluble |
| | | | 0 hours | Partially soluble |
| | | | 1 hours | Partially soluble |
| | 100 | 0.9% Sodium chloride (saline) | 0 hours | Insoluble |
| | | Distilled Water | 1 hours | Insoluble |
| | | | 0 hours | Partially soluble |
| | | | 1 hours | Insoluble |
| | 200 | 0.9% Sodium chloride (saline) | 0 hours | Insoluble |
| | | Distilled Water | 1 hours | Insoluble |
| | | | 0 hours | Insoluble |
| | | | 1 hours | Insoluble |
| mono-Hydrochloride by the method of Brana et al. | 50 | 0.9% Sodium chloride (saline) | 0 hours | Partially soluble |
| | | Distilled Water | 1 hours | Partially soluble |
| | | | 0 hours | Partially soluble |
| | | | 1 hours | Partially soluble |
| | 100 | 0.9% Sodium chloride (saline) | 0 hours | Insoluble |
| | | Distilled Water | 1 hours | Insoluble |
| | | | 0 hours | Partially soluble |
| di-Hydrochloride | 50 | 0.9% Sodium chloride (saline) | 0 hours | Insoluble |
| | | Distilled Water | 1 hours | Insoluble |
| | | | 0 hours | Partially soluble |
| | | | 1 hours | Partially soluble |
| | 100 | 0.9% Sodium chloride (saline) | 0 hours | Insoluble |
| | | Distilled Water | 1 hours | Insoluble |
| | | | 0 hours | Insoluble |
| | | | 1 hours | Insoluble |

TABLE 4-continued

| AMONAFIDE SALT | Amount of Amonafide Salt (mg) | Solvent | Timepoint | Dissolution Status |
|---|---|---|---|---|
| L-Malate | 50 | 0.9% Sodium chloride (saline) | 0 hours | Soluble |
| | | Distilled Water | 1 hours | Soluble |
| | | | 0 hours | Soluble |
| | | | 1 hours | Soluble |
| | 100 | 0.9% Sodium chloride (saline) | 0 hours | Soluble |
| | | Distilled Water | 1 hours | Soluble |
| | | | 0 hours | Soluble |
| | | | 1 hours | Soluble |
| | 200 | 0.9% Sodium chloride (saline) | 0 hours | Soluble |
| | | Distilled Water | 1 hours | Soluble |
| | | | 0 hours | Soluble |
| | | | 1 hours | Soluble |
| Pyruvate | 50 | 0.9% Sodium chloride (saline) | 0 hours | Soluble |
| | | Distilled Water | 1 hours | Soluble |
| | | | 0 hours | Soluble |
| | | | 1 hours | Soluble |
| | 100 | 0.9% Sodium chloride (saline) | 0 hours | Soluble |
| | | Distilled Water | 1 hours | Soluble |
| | | | 0 hours | Soluble |
| | | | 1 hours | Soluble |
| | 200 | 0.9% Sodium chloride (saline) | 0 hours | Partially Soluble |
| | | Distilled Water | 1 hours | Partially Soluble |
| | | | 0 hours | Soluble |
| | | | 1 hours | Soluble |
| Tartrate | 50 | 0.9% Sodium chloride (saline) | 0 hours | Soluble |
| | | Distilled Water | 1 hours | Soluble |
| | | | 0 hours | Soluble |
| | | | 1 hours | Soluble |
| | 100 | 0.9% Sodium chloride (saline) | 0 hours | Soluble |
| | | Distilled Water | 1 hours | Soluble |
| | | | 0 hours | Soluble |
| | | | 1 hours | Soluble |
| | 200 | 0.9% Sodium chloride (saline) | 0 hours | Soluble |
| | | Distilled Water | 1 hours | Soluble |
| | | | 0 hours | Soluble |
| | | | 1 hours | Soluble |
| Glycolate | 50 | 0.9% Sodium chloride (saline) | 0 hours | Soluble |
| | | Distilled Water | 1 hours | Soluble |
| | | | 0 hours | Soluble |
| | | | 1 hours | Soluble |
| | 100 | 0.9% Sodium chloride (saline) | 0 hours | Soluble |
| | | Distilled Water | 1 hours | Soluble |
| | | | 0 hours | Soluble |
| | | | 1 hours | Soluble |
| | 200 | 0.9% Sodium chloride (saline) | 0 hours | Soluble |
| | | Distilled Water | 1 hours | Soluble |
| | | | 0 hours | Soluble |
| | | | 1 hours | Soluble |

From the data in Table 4, it is evident that a number of organic acid salts of amonafide are more soluble in distilled water and in saline at high concentration than either of the corresponding hydrochloride salt forms. These latter include the aspartate, malate, pyruvate, oxo-glutarate and tartrate. It is also notable that regardless of method of preparation, the monohydrochloride salts show consistently inferior solubility when compared to representative organic salts.

EXAMPLE 5
Amonafide Malate has Anti-Cancer Activity In Vitro

Amonafide Malate was tested for cytotoxic activity in a panel of three cell lines, MCF7 (Breast), H460 (Non-Small Cell Lung Cancer) and SF268 (Glioma). These cell lines are used by the National Cancer Institute: Developmental Therapeutics Branch in their preliminary screening process for antineoplastic agents. Subsequently, Amonafide Malate was tested against a larger panel of breast, lung and colon cell lines

| Breast: | MCF-7, BT474, MDA-231, T47D and SKBr3 |
|---|---|
| Colon: | HT29, HCT116 and COLO205 |
| Lung: | H460, H23 and A549 |
| Prostate: | DU-145, PC-3 and LNCaP |

The following protocol was used:

Cells were grown in RPMI 1640 medium containing 5% fetal bovine serum and 2 mM L-glutamine. Dependent upon cell doubling time, between 5,000 and 40,000 cells were inoculated into 96 well microtiter plates in a volume of 100 uL per well. The plates were incubated at 37° C., 5% $CO_2$, 95% air, and 100% relative humidity for 24 hours prior to the addition of the experimental drug. After the, 24 hour incubation, two (2) plates of each cell line were fixed in situ with trichloroacetic acid (TCA) to establish the cell population at time of drug addition (Tz).

Prior to use, the experimental drugs were solubilized in dimethyl sulfoxide at 400-fold the desired final maximum test concentration and frozen. At time of drug addition, an aliquot of frozen concentrate was thawed and diluted to twice the desired final maximum test concentration with complete medium containing 50 ug/ml gentamicin. An additional four (4) 10-fold or ½ log serial dilutions was made for a total of five (5) drug concentrations plus a control. An aliquot of 100 ul of each drug dilution was added to the appropriate well that already contains 100 ul of medium containing the cells. The plates were then incubated for 48 hours at 37° C., 5% $CO_2$; 95% air and 100% relative humidity.

The number of viable cells was estimated by either a SRB or MTT calorimetric assays.

For SRB assay, cells were fixed in situ by the gentle addition of 50 ul cold (w/v) TCA (final concentration, 10% TCA) and incubated for 60 minutes at 4° C. The supernatant was discarded, plates washed five (5) times with tap water and air dried. Then Sulforhodamine B (SRB) solution (100 µl) at a 0.4% (w.v.) in 1% acetic acid was added to each well, and the plates incubated for 10 minutes at room temperature. Unbound dye was removed by washing five (5) times with 1% acetic acid and the plates were air dried. The bound stain was solubilized with 10 mM trizma base and the absorbance was read on an automated plate reader at a wavelength of 515 nm.

The MTT assay measures the ability of viable cells to reduce a tetrazolium salt (MTT) to an insoluble form, a formazan salt. For MTT analysis 20 µl of MTT solution (5 mg/ml in PBS) was added to each well containing cells. The plate was incubated at 37° C. for 5 hours. Media was removed with needle and syringe. 200 µl of DMSO was added to each well and pipetted up and down to dissolve crystals. Plate was placed into a 37° C. incubator for 5 minutes to dissolve air bubbles. Absorbance was read on an automated plate reader at a wavelength of 550 nm.

Percent net growth inhibition, as shown in FIGS. 2–7, was calculated using the seven absorbance measurements: absorbance by cells at time zero (Tz), absorbance by cells grown in the absence of drug (C), and absorbance of cells grown at the five drug concentrations (Ti). The following expression was used:

% Net Growth=[(Ti−Tz)/(C−Tz)]×100 if Ti was greater than or equal to Tz.

% Net Growth=[(Ti−Tz)/Tz]×100 if Ti was less than Tz.

Using the plot of Percent Net Growth as a function of drug concentration, lethality concentration "50%" ($LC_{50}$), total growth inhibition (TGI) and growth inhibition "50%" ($GI_{50}$) were determined as follows.

TGI was determined as the concentration of Amonafide malate at which Percent Net Growth was 0%. $GI_{50}$ was determined as the concentration of Amonafide malate at which Percent Net Growth was 50%. $LC_{50}$ was determined as the concentration of Amonafide malate at which Percent Net Growth was −50%.

Figure 2:
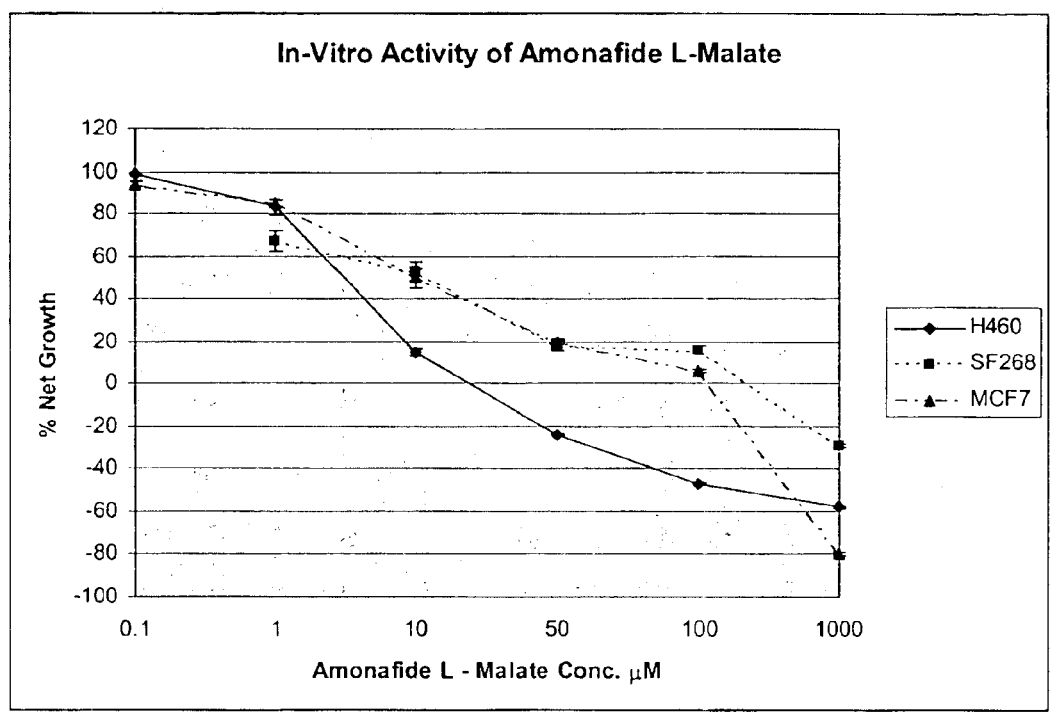
FIG. 2 is a graph showing the percent net cell growth of cancer cell from the cell lines H460 (♦), SF268 (■) and MCF7 (▲) in the presence of varying concentrations of amonafide malate. The concentration of amonafide malate is given in μM.
Figure 3:
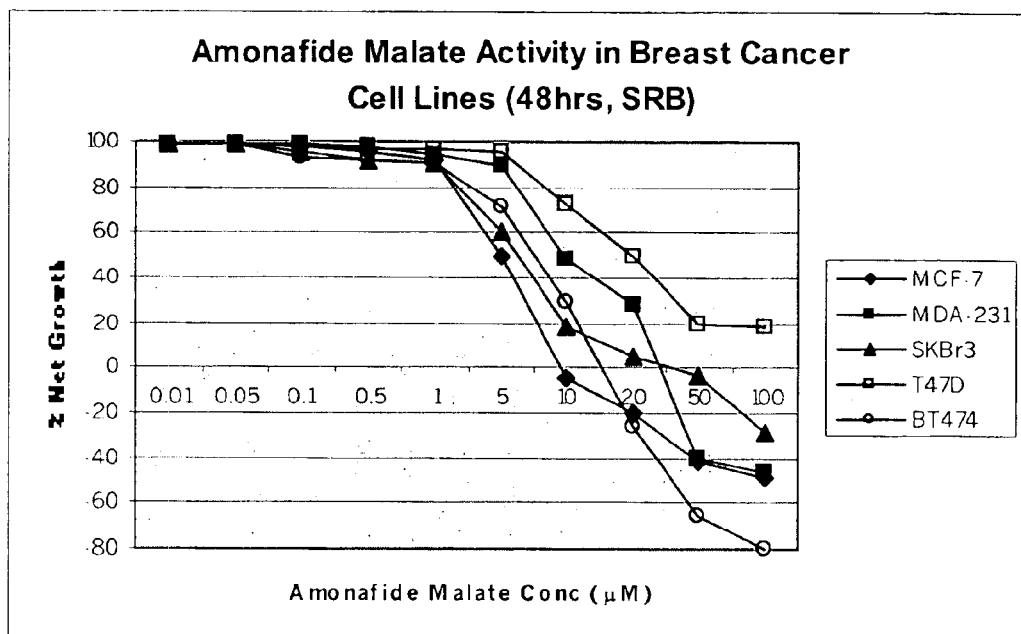
FIG. 3 is a graph showing the percent net cell growth of breast cancer cell from the cell lines MCF-7 (♦), BT474 (○), MDA-231 (■), T47D (□) and SKBr3 (▲) using Sulforhodamine B analysis in the presence of varying concentrations of amonafide malate. The concentration of amonafide malate is given in μM.
Figure 4:
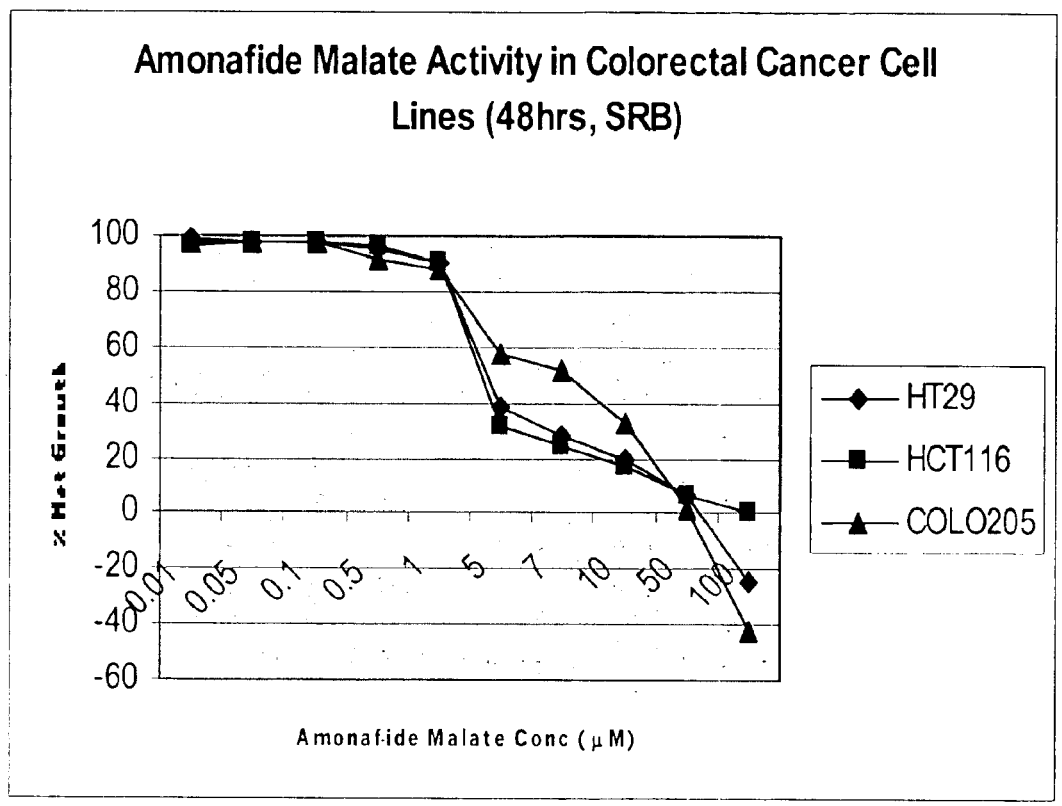
FIG. 4 is a graph showing the percent net cell growth of colorectal cancer cell from the cell lines HT29(♦), HCT116 (■) and COLO205 (▲) using Sulforhodamine B analysis in the presence of varying concentrations of amonafide malate. The concentration of amonafide malate is given in μM.
Figure 5:
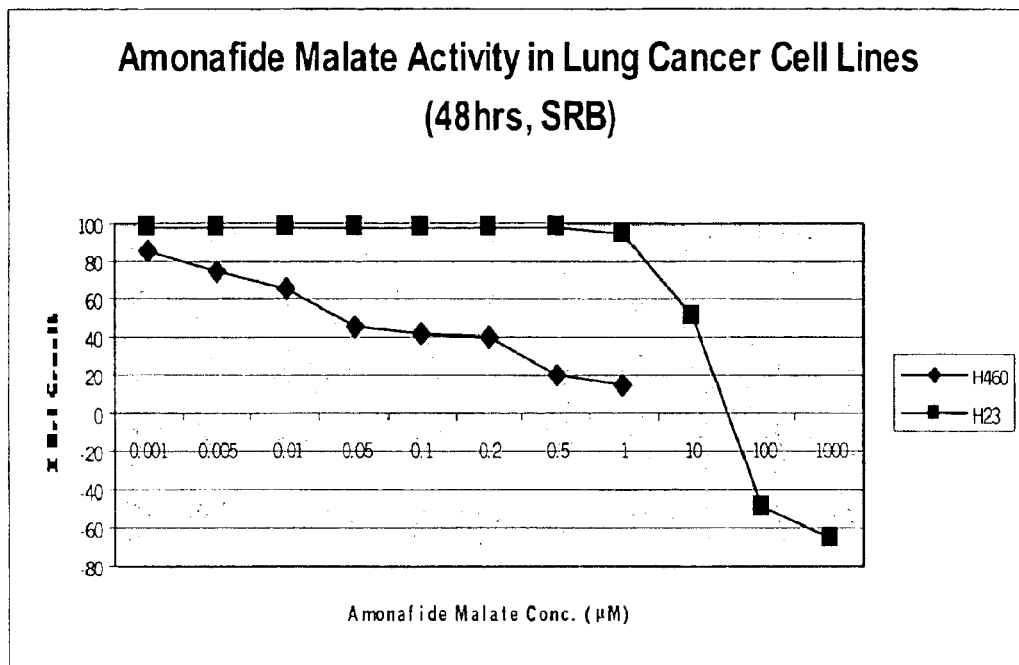
FIG. 5 is a graph showing the percent net cell growth of lung cancer cell from the cell lines H460 (♦) and H23 (■) using Sulforhodamine B analysis in the presence of varying concentrations of amonafide malate. The concentration of amonafide malate is given in μM.
Figure 6:
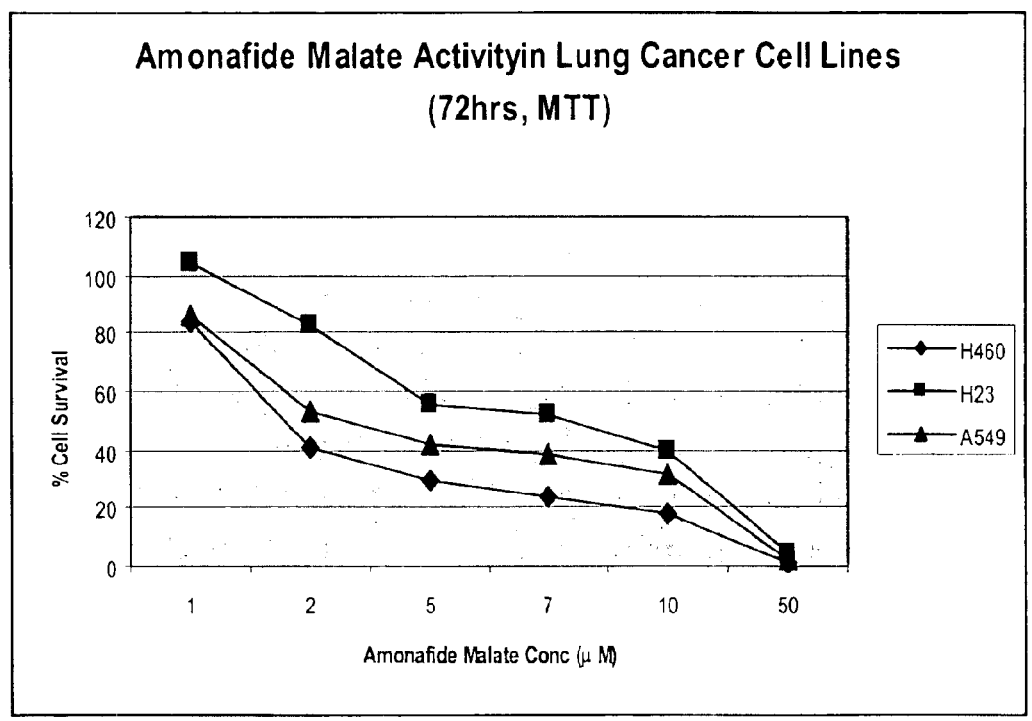
FIG. 6 is a graph showing the percent net cell growth of lung cancer cell from the cell lines H460 (♦), H23 (■) and A549 (▲) using MTT analysis in the presence of varying concentrations of amonafide malate. The concentration of amonafide malate is given in μM.

As can be seen in FIG. 2, Amonafide malate significantly affected the growth rate of cell lines H-460 (non-small cell lung carcinoma), SF-268 (glioblastoma) and MCF-7 (breast cancer) resulting in $GI_{50}$ of between 4 and 8 µM. The data presented in Table 5 summarizes the results shown in FIG. 2

TABLE 5

|  | H460 | SF268 | MCF7 |
|---|---|---|---|
| $GI_{50}$ (M) | 4.11E−06 | 7.70E−06 | 5.16E−06 |
| TGI (M) | 0.96E−04 | 1.54E−04 | 1.10E−04 |
| $LC_{50}$ (M) | 1.70E−04 | 8.42E−04 | 6.62E−04 |

Figure 7:
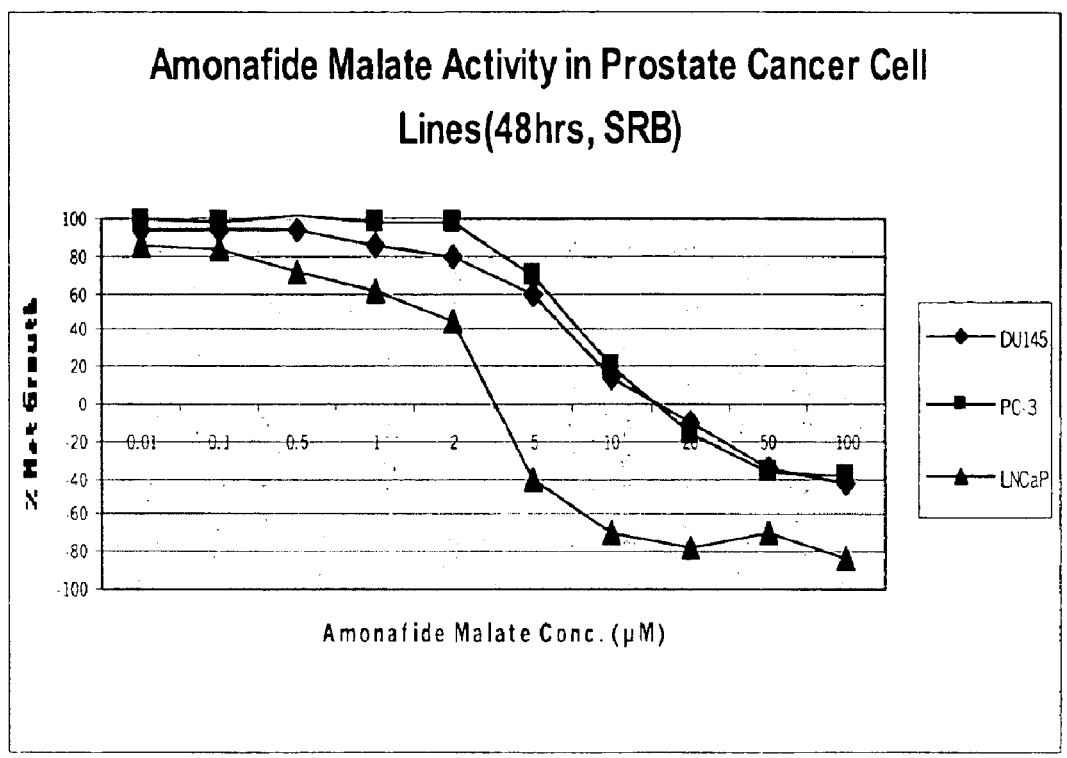
FIG. 7 is a graph showing the percent net cell growth of prostate cancer cell from the cell lines DU-145 (♦), PC-3 (■) and LNCaP (▲) using Sulforhodamine B analysis in the presence of varying concentrations of amonafide malate. The concentration of amonafide malate is given in μM.

FIGS. 3 to 7 present data for panels of cell lines derived from breast cancer (FIG. 3), colorectal cancer (FIG. 4), lung cancer (FIG. 5, using SRB assay, and FIG. 6, using MTT assay) and prostate cancer (FIG. 7). As can be seen, reduction of net growth by as much as 50% or better was achieved at Amonafide malate concentrations between about 5 and about 10 µM.

EXAMPLE 6

Amanofide has Anti-Cancer Activity In Vivo

Amonafide Malate was tested for in vivo anti-cancer activity in models of three different solid tumor types, MCF7 and MDA-231 (Breast), COLO205 (Colorectal) and PC3 (Prostate). The in vivo activity was tested using the Hollow Fiber methodology developed by the National Cancer Institute: Developmental Therapeutics Branch for use in their antineoplastic agent screening program. Specifically, the anti-cancer activity of amonafide L-malate was tested by the following protocol.

Polyvinylidene fluoride (PVDF) hollow fibers were used. The fibers were individually flushed and filled with 70% ethanol and incubated in 70% ethanol at room temperature for a minimum of 96 hour. Following three washes with deionized water, the fibers were filled with and placed into a pan of deionized water for sterilization by autoclaving. Then the fibers were stored in water at 4° C. until used.

Mice were grouped into 4 groups, two control groups with 6 mice per group and 2 experimental groups with 3 mice per group. The experimental groups were as follows:

Group A: Control, hollow fibers without cells

Group B: Control, hollow fibers for 3 cell lines without drug treatment

Group C: hollow fibers for 3 cell lines+Amonafide Malate

Anesthesia was induced in mice by ketamine/acepromazine/xylazine injected intraperitoneally (i.p.) For the intraperitoneal (i.p.) implants, a small incision was made through the skin and musculature of the dorsal abdominal wall, the fiber samples were inserted into the peritoneal cavity in a craniocaudal direction and the incision was closed with a skin staple. For subcutaneous (s.c.) implants, a small skin incision was made at the nape of the neck to allow insertion of an 11 gauge tumor implant trocar. The trocar, containing the hollow fiber samples, was inserted caudally through the subcutaneous tissues and the fibers were deposited during withdrawal of the trocar. The skin incision was closed with a skin staple. Each mouse was host of 6 samples, representing 3 tumor cells lines each of which was cultured in the 2 physiologic compartments (i.p. and s.c.).

In a first series of experiments, Amonafide Malate (29.4 mg/kg) was injected intraperitoneally (i.p.), once daily on days 3–8. In a second series of experiments, Amonafide Malate was administered i.p. twice-daily at either 15 mg/kg or 29 mg/kg.

On the day following the last drug injection, the animals were sacrificed and the hollow fibers extracted. The hollow fibers were then subjected to the stable endpoint MTT assay as described in Example 5. The optical density of each sample is determined spectrophotometrically at 540 nm and the mean of each treatment group is calculated. The percent net growth for each cell line in each treatment group is calculated as described in Example 5 and compared to the percent net growth in the vehicle treated controls (Group B) using the formula below to determine the percent growth inhibition:

$$\% \text{ growth inhibition} = (\text{Net Growth}_{Control} - \text{Net Growth}_{Treated})/\text{Net Growth}_{Control} * 100$$

Individual mouse body weights were recorded daily and animals were monitored daily for general health for 6 days. It was not necessary to sacrifice any animals in a $CO_2$ chamber prematurely as a result of a body weight loss of greater than 20%, or as a result of evidence of other signs of toxicity.

Figure 8:
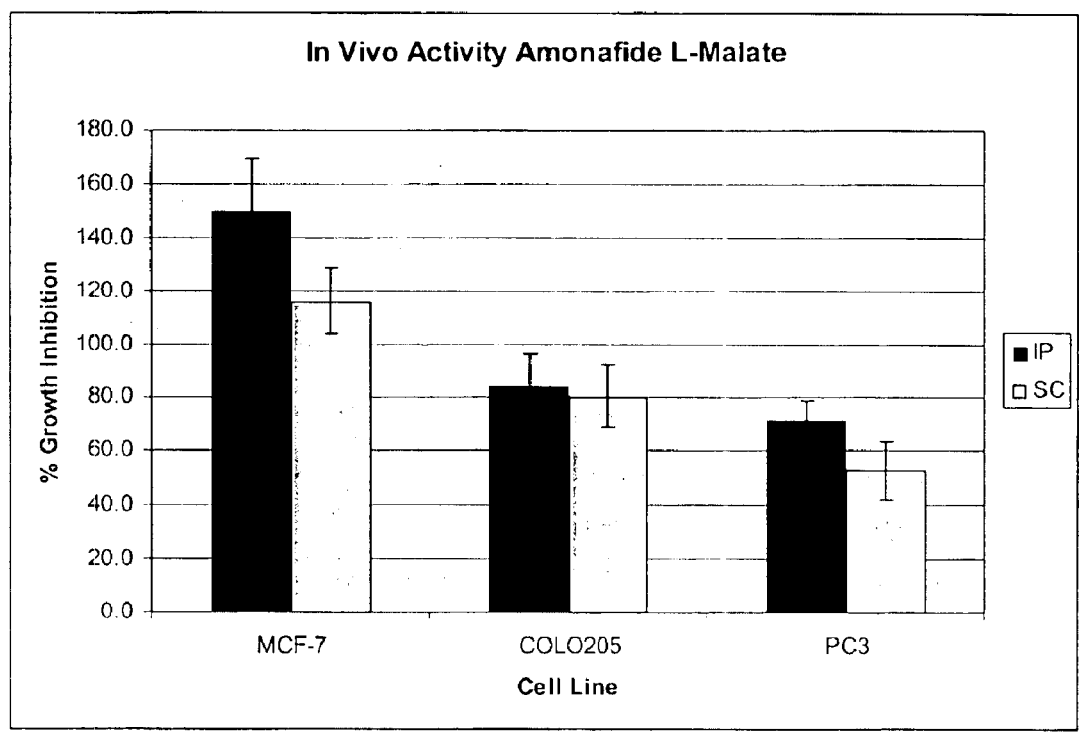
FIG. 8 is a graph showing the percent growth inhibition by amonafide malate of MCF-7, COLO205 and PC3 tumors in mice. Amonafide malate was administered intraperitoneally (IP) or subcutaneously (SC).
Figure 9:
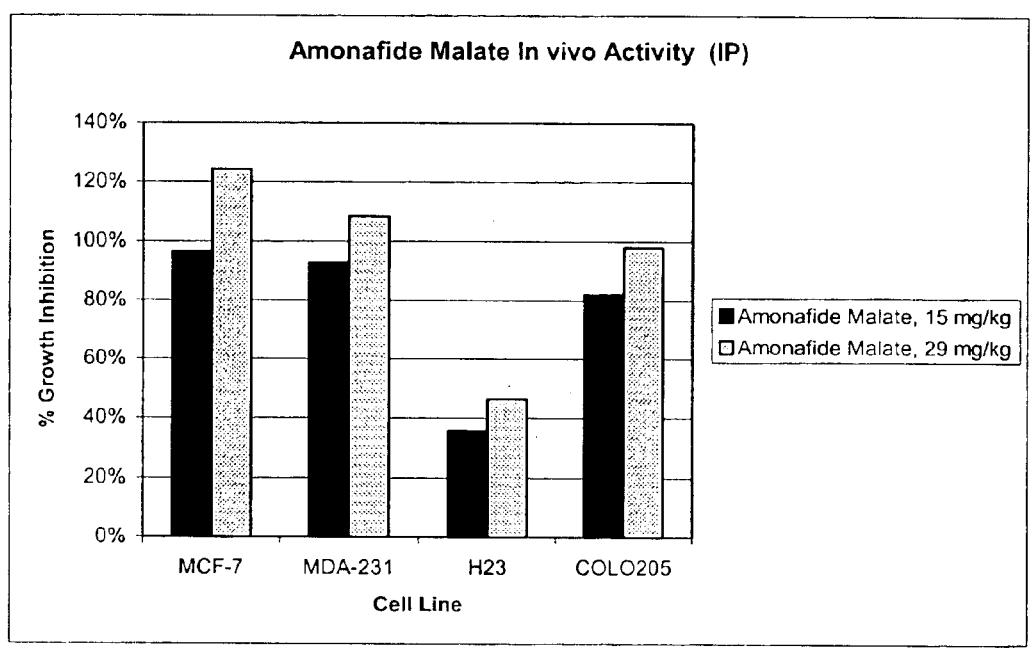
FIG. 9 is a graph showing in vivo percent growth inhibition of intraperitoneally implanted solid tumor by amonafide malate in mice. Cell lines used were MCF-7, MDA-231, H23 and COLO205. Amonafide malate was administered intraperitoneally twice-daily at either 15 mg/kg or 29 mg/kg.
Figure 10:
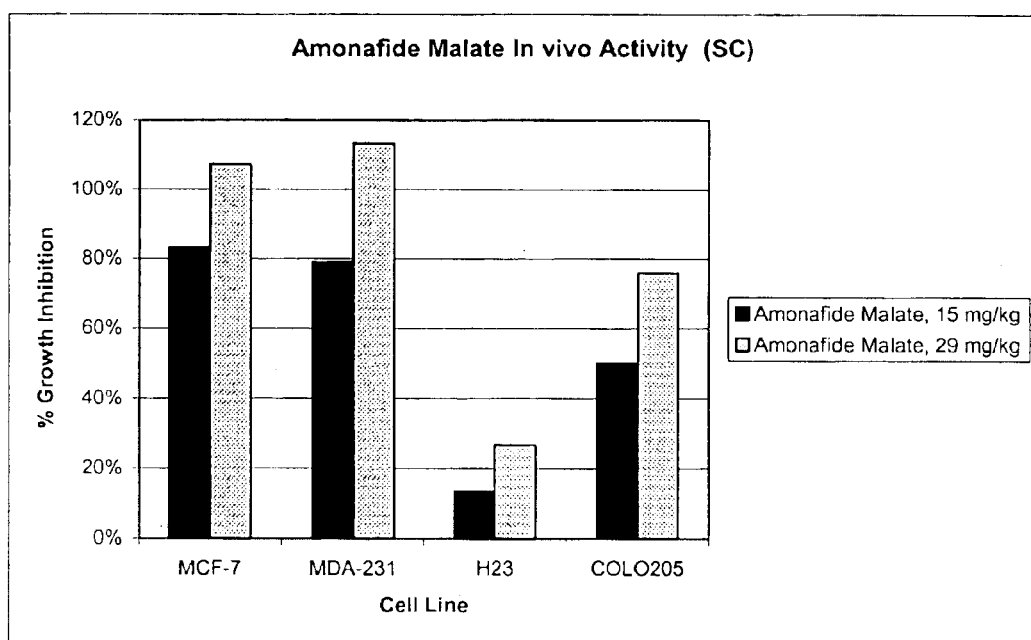
FIG. 10 is a graph showing in vivo percent growth inhibition of intraperitoneally implanted solid tumor by amonafide malate in mice. Cell lines used were MCF-7, MDA-231, H23 and COLO205. Amonafide malate was administered intraperitoneally twice-daily at either 15 mg/kg or 29 mg/kg.

FIG. 8 and Table 6 show data for once-daily administration of 29.4 mg/kg of Amonafide Malate. FIGS. 9 and 10 and Tables 7 and 8 show data for twice-daily administration of Aminofide Malate at either 15 mg/kg or 29 mg/kg.

As presented in Tables 6–8 and FIG. 10, Amonafide malate showed considerable activity, resulting in percent growth inhibition of above 100% (indicating lethality for cancerous cells) for cell lines MCF-7 and MDA-231 (breast cancer). Significant percent growth inhibition was achieved in cell lines PC-3 (prostate) and COLO205 (colorectal cancer).

TABLE 6

|  | IP | | SC | |
| --- | --- | --- | --- | --- |
|  | % Growth Inhibition | STDEV | % Growth Inhibition | STDEV |
| MCF-7 | 150.2 | 19.2 | 116.1 | 12.1 |
| COLO205 | 84.6 | 11.7 | 80.4 | 11.7 |
| PC3 | 71.6 | 7.3 | 52.9 | 10.9 |

TABLE 7

| | | I.P. fibers % Growth Inhibition | |
| --- | --- | --- | --- |
| Cell line Type | Name | Amonafide Malate, 15 mg/kg | Amonafide Malate, 29 mg/kg |
| Breast | MCF-7 | 97% | 124% |
| Breast | MDA-231 | 93% | 108% |
| Lung | H23 | 36% | 47% |
| Colon | COLO205 | 82% | 98% |

TABLE 8

| | | S.C. fibers % Growth Inhibition | |
| --- | --- | --- | --- |
| Cell line Type | Name | Amonafide Malate, 15 mg/kg | Amonafide Malate, 29 mg/kg |
| Breast | MCF-7 | 83% | 107% |
| Breast | MDA-231 | 79% | 113% |
| Lung | H23 | 13% | 27% |
| Colon | COLO205 | 50% | 76% |

While this invention has been particularly shown and described with references to preferred embodiments thereof, it will be understood by those skilled in the art that various changes in form and details may be made therein without departing from the scope of the invention encompassed by the appended claims.

What is claimed is:

1. A pharmaceutical composition comprising a pharmaceutically acceptable carrier or diluent and amonafide malate.

2. The composition of claim 1 wherein amonafide is in the monovalent form.

3. A pharmaceutical composition comprising a pharmaceutically acceptable carrier or diluent and amonafide glycolate.

4. The composition of claim 3 wherein amonafide is in the monovalent form.

5. A method of treating a subject with breast cancer, comprising the step of administering to the subject an effective amount of amonafide malate or amonafide glycolate.

6. The method of claim 5 wherein amonafide is in the monovalent form.

7. A method of treating a subject with colon cancer, comprising the step of administering to the subject an effective amount of amonafide malate or amonafide glycolate.

8. The method of claim 7 wherein amonafide is in the monovalent form.

9. A method of treating a subject with lung cancer, comprising the step of administering to the subject an effective amount of amonafide malate or amonafide glycolate.

10. The method of claim 9 wherein amonafide is in the monovalent form.

11. A method of treating a subject with prostate cancer, comprising the step of administering to the subject an effective amount of amonafide malate or amonafide glycolate.

12. The method of claim 11 wherein amonafide is in the monovalent form.

13. A method of treating a subject with leukemia, comprising the step of administering to the subject an effective amount of amonafide malate or amonafide glycolate.

14. The method of claim 13 wherein amonafide is in the monovalent form.

* * * * *